(12) United States Patent
Kulkarni

(10) Patent No.: US 11,793,684 B2
(45) Date of Patent: Oct. 24, 2023

(54) FOLDED INDIVIDUAL ARTICLE IN A CIRCULAR PACKAGE

(71) Applicant: Johnson & Johnson Consumer Inc., Skillman, NJ (US)

(72) Inventor: Sarika Kulkarni, Santa Clarita, CA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 977 days.

(21) Appl. No.: 16/625,175

(22) PCT Filed: Jun. 28, 2018

(86) PCT No.: PCT/IB2018/054816
§ 371 (c)(1),
(2) Date: Dec. 20, 2019

(87) PCT Pub. No.: WO2019/003183
PCT Pub. Date: Jan. 3, 2019

(65) Prior Publication Data
US 2020/0138645 A1    May 7, 2020

Related U.S. Application Data

(60) Provisional application No. 62/527,191, filed on Jun. 30, 2017.

(51) Int. Cl.
*A61F 13/472* (2006.01)
*A61F 13/551* (2006.01)
*A61F 13/47* (2006.01)
(52) U.S. Cl.
CPC ...... *A61F 13/5514* (2013.01); *A61F 13/4704* (2013.01); *A61F 13/47236* (2013.01)

(58) Field of Classification Search
CPC ...... A61F 2013/4568; A61F 2013/4581; A61F 2013/4543; A61F 2013/455;
(Continued)

(56) References Cited

U.S. PATENT DOCUMENTS 3,683,915 A    8/1972    Voss
3,971,378 A    7/1976    Krantz
(Continued)

FOREIGN PATENT DOCUMENTS

AU    2009213760 B    8/2009
EP    471384 A    2/1992
(Continued)

OTHER PUBLICATIONS

International search report dated Oct. 8, 2018, for international application PCT/IB2018/054816.
(Continued)

*Primary Examiner* — Bradley H Philips

(57) ABSTRACT

A packaged elongate sanitary protection product includes a folded sanitary protection product enveloped in a substantially circular package and having first and second arcuate end portions comprising first and second ends, respectively, separated by a central portion. The topsheet and backsheet are joined in a flange surrounding the absorbent structure, and the absorbent structure comprises at least three intersecting, substantially circular sections aligned along a longitudinal axis. A first circular section is associated with the first arcuate end portion, and a second section is associated with the second arcuate end portion, and a central portion is associated with at least one intervening substantially circular portion. The intersections define folding axes perpendicular to the longitudinal axis and enlarged flange sections of the topsheet and backsheet. The product is folded at the fold
(Continued)

lines and the enlarged flange sections are folded inwardly to give the product a generally circular form.

3 Claims, 5 Drawing Sheets

(58) Field of Classification Search
CPC .... A61F 2013/4556; A61F 2013/53409; A61F 2013/53418; A61F 2013/53427; A61F 13/55135–55145; A61F 13/5516–55165; A61F 13/4704; A61F 13/47236; A61F 13/47245–47254
See application file for complete search history.

(56) References Cited

U.S. PATENT DOCUMENTS

| | | | |
|---|---|---|---|
| 4,556,146 | A | 12/1985 | Swanson et al. |
| 4,560,379 | A | 12/1985 | Stemmler |
| 4,650,480 | A | 3/1987 | Stemmler |
| 4,674,510 | A | 6/1987 | Sneider |
| 4,692,162 | A | 9/1987 | Binker et al. |
| 4,765,477 | A | 8/1988 | Froidh et al. |
| 4,917,675 | A | 4/1990 | Taylor et al. |
| 5,827,248 | A | 10/1998 | Crawford |
| 5,891,123 | A | 4/1999 | Balzar |
| 6,036,679 | A | 3/2000 | Balzar et al. |
| 6,293,932 | B1 | 9/2001 | Balzar et al. |
| 6,502,695 | B1 | 1/2003 | Kim et al. |
| 6,551,431 | B2 | 4/2003 | Lee |
| 6,908,458 | B1 | 6/2005 | Sauer et al. |
| 7,017,744 | B2 | 3/2006 | Persson |
| 7,181,894 | B2 | 2/2007 | Snell |
| 8,142,255 | B2 | 3/2012 | Johnston |
| 9,242,788 | B2 | 1/2016 | Gagliardi et al. |
| 9,278,035 | B2 | 3/2016 | Hashino et al. |
| 2002/0063076 | A1 | 5/2002 | Kolterjohn et al. |
| 2004/0250712 | A1 | 12/2004 | Tippey |
| 2006/0100599 | A1 | 5/2006 | Engel et al. |
| 2008/0077114 | A1* | 3/2008 | Klippen ............ A61F 13/55135 604/389 |
| 2010/0036355 | A1* | 2/2010 | Hakansson ......... A61F 13/4704 604/385.21 |
| 2013/0220860 | A1 | 8/2013 | Bacon et al. |
| 2014/0367290 | A1 | 12/2014 | Nomoto et al. |
| 2015/0313763 | A1 | 11/2015 | Bagger-Sjoback et al. |
| 2016/0228309 | A1* | 8/2016 | Ekstedt ............... A61F 13/5514 |

FOREIGN PATENT DOCUMENTS

| | | | |
|---|---|---|---|
| EP | 750896 | A | 1/1997 |
| EP | 754440 | A | 1/1997 |
| EP | 841049 | A | 5/1998 |
| EP | 1119325 | A | 8/2001 |
| EP | 1324735 | A | 7/2003 |
| EP | 1357877 | A | 11/2003 |
| EP | 1392213 | A | 3/2004 |
| EP | 1392580 | A | 3/2004 |
| EP | 1793779 | A | 6/2007 |
| EP | 1934102 | A | 6/2008 |
| EP | 1959903 | A | 8/2008 |
| EP | 2046253 | A | 4/2009 |
| EP | 2379038 | A | 10/2011 |
| EP | 2512943 | A | 10/2012 |
| EP | 2689757 | A | 1/2014 |
| EP | 2796119 | A | 10/2014 |
| WO | WO 1996/020668 | A | 7/1996 |
| WO | WO 1997/015261 | A | 5/1997 |
| WO | WO 1998/020823 | A | 5/1998 |
| WO | WO 1998/053781 | A | 12/1998 |
| WO | WO 1999/052484 | A | 10/1999 |
| WO | WO 2000/013622 | A | 3/2000 |
| WO | WO 2000/021477 | A | 4/2000 |
| WO | WO 2001/012117 | A | 2/2001 |
| WO | WO 2012/102071 | A | 8/2012 |
| WO | WO 2013/077789 | A | 5/2013 |
| WO | WO 2013/162430 | A | 10/2013 |
| WO | WO 2014/204018 | A | 12/2014 |
| WO | WO 2015/060755 | A | 4/2015 |

OTHER PUBLICATIONS

YouTube video clip entitled "Classic double bed mosquito net Folding method-I," Screen captures and translated transcript, 13 pages, uploaded on Jul. 3, 2016 by user "Classic mosquito net", retrieved from Internet https://www.youtube.com/watch?v=pcmyYOqzYUI.

* cited by examiner

FOLDED INDIVIDUAL ARTICLE IN A CIRCULAR PACKAGE

CROSS-REFERENCE TO RELATED APPLICATIONS

This application is the national stage filing under 35 USC 371 of international application PCT/IB2018/054816 filed on Jun. 28, 2018, which claims the benefit of U.S. provisional application 62/527191 filed on Jun. 30, 2017.

FIELD OF THE INVENTION

The present invention relates to a foldable consumer article in a single use package with a generally circular appearance. More specifically, the present invention is directed to a consumer article with circular ends folded in "Z" configurations and individually wrapped in a thin, rounded sealable package.

BACKGROUND OF THE INVENTION

Personal consumer products such as wipes, wound bandages, and absorbent articles are commonly packaged in packages containing many individual articles. Often, the consumer wishes only to carry one or several of the articles in in a pocket, small bag, or purse. For user convenience, the articles may be packaged individually in single-use packages. Typically, the package is foil or plastic material, and sealed to prevent contamination of the product.

Generally, the package is square or rectangular in geometry. In some cases, the article is folded so as to take up less space in the bag or purse.

In the case of absorbent articles such as sanitary napkins and panty liners, women will carry one or several in their bag or purse. They remove them when needed. The square or rectangular packages, however, provide a conspicuous presentation for a single wrapped and folded sanitary article, and many women desire a less conspicuous wrapper, such as a more circular product.

Unfortunately, packaging a folded sanitary product having one or more protruding square edges does not present a nice, circular product for wrapping, and it creates wasted area within a circular package; this is especially true for a folded product employing a "C-fold" or G-fold" configuration. Therefore, what is needed is a substantially circular, folded sanitary product that can be neatly and economically enveloped in a circular pouch.

SUMMARY OF THE INVENTION

Surprisingly, we have found that a sanitary product can be designed to be folded to form a substantially circular, folded sanitary product that can be neatly enveloped in a tight-fitting circular pouch.

In particular, a packaged elongate sanitary protection product includes a folded sanitary protection product enveloped in a substantially circular package. The elongate sanitary protection has a topsheet, a backsheet, and an absorbent structure therebetween and having a longitudinal axis and a thickness, first and second arcuate end portions comprising first and second ends, respectively, separated by a central portion enveloped in a substantially circular package. The arcuate end portions have an effective radius and a pair of substantially parallel longitudinal side edges connecting the first and second ends. The topsheet and backsheet are joined together in a flange surrounding the absorbent structure, and the absorbent structure comprises at least three intersecting, substantially circular sections aligned along the longitudinal axis. A first substantially circular section is associated with the first arcuate end portion, and a second substantially circular section is associated with the second arcuate end portion, and a central portion is associated with at least one intervening substantially circular portion. The intersections of adjacent substantially circular sections define folding axes perpendicular to the longitudinal axis and enlarged flange sections of the topsheet and backsheet. The sanitary protection product is folded at the fold lines and the enlarged flange sections are additionally folded inwardly, approximately 45° to form a folded sanitary protection product having a generally circular form.

DETAILED DESCRIPTION OF THE INVENTION

The present invention relates to foldable absorbent sanitary articles in a package with a generally circular appearance. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

The foldable disposable sanitary articles are first folded along at least two folding axes, also known as a "Z-fold", and then packaged in a thin, generally circular package.

Figure 1:
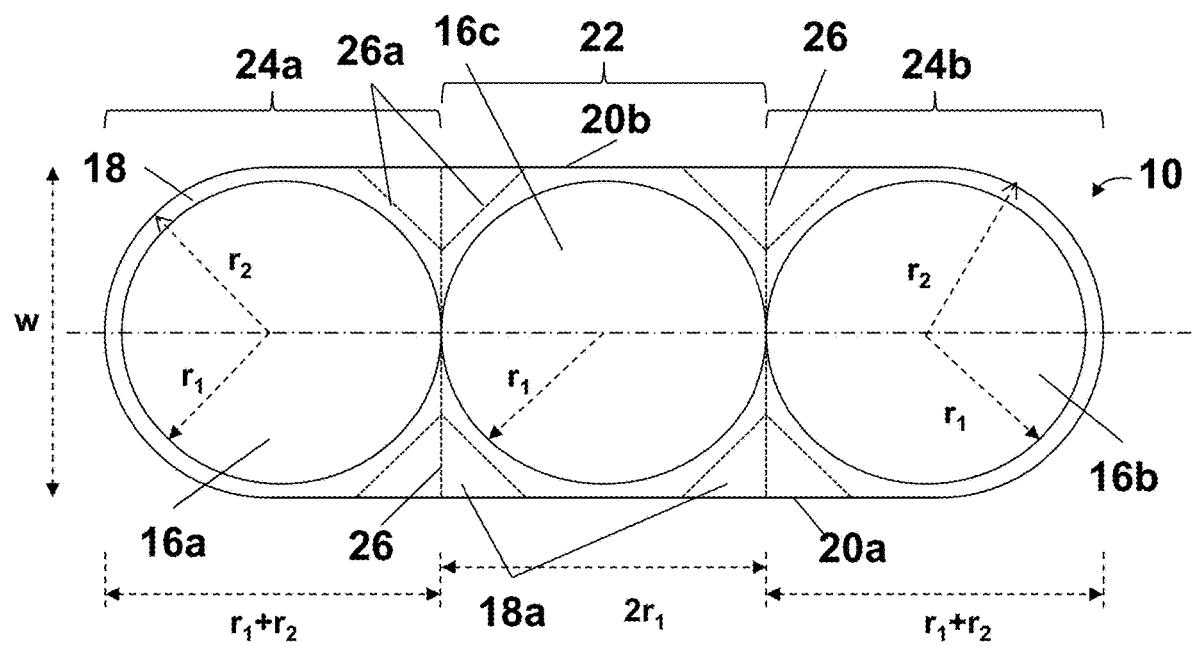
FIG. 1 is a top view of an embodiment of a foldable, round-ended consumer article of the present invention.
Figure 2:
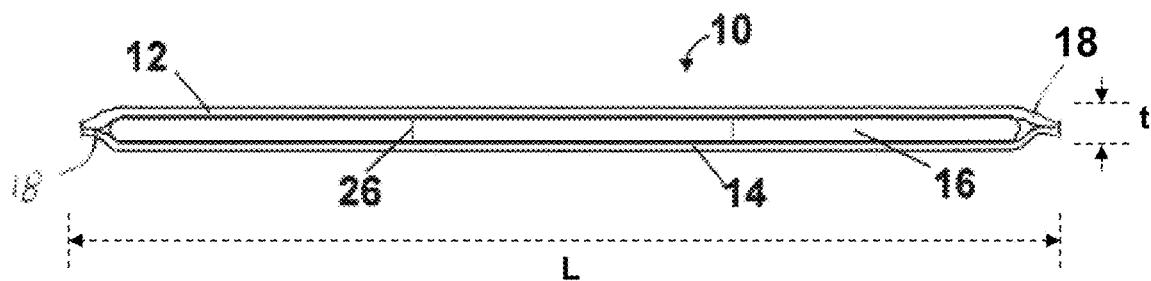
FIG. 2 is a side view of the consumer article embodiment of FIG. 1.

Referring to the drawings, FIGS. 1 and 2 are top and cross-sectional views, respectively, of an embodiment of a foldable, round-ended absorbent sanitary article 10 which has a topsheet 12, a backsheet 14, and an absorbent structure 16 therebetween. The topsheet 12 and backsheet 14 are joined together in a flange 18 surrounding the absorbent structure 16 to form a product having a thickness (as measured using the procedure described below). Preferably, the product has a thickness of less than about 2.5 mm. The article has a first longitudinal side 20a, and a second longitudinal side 20b. Article 10 also has a central portion 22 and first and second arcuate end portions 24a and 24b, respectively.

The materials of the topsheet, backsheet, and absorbent structure may be any conventional or exotic sanitary protection materials. Optional materials, such as transfer layers, may also be included in the absorbent sanitary articles of this invention.

The absorbent structure 16 comprises at least three intersecting, substantially circular sections aligned along the longitudinal axis, a first substantially circular section 16a is associated with the first arcuate end portion 24a and the second substantially circular section 16b associated with the second arcuate end portion 24b. While the embodiment of FIGS. 1-2 includes only three substantially circular portions and the third substantially circular portion 16c is shown in the central portion 22, alternative embodiments, described later, may incorporate additional circular portions of the absorbent structure in an elongated central portion.

As shown in FIGS. 1-2, the three substantially circular portions 16a-16c of are equal sized circles of radius $r_1$, and the arcuate end portions are defined by the radius $r_2$ of the flange 18 extending around the absorbent structure 16. Thus, the length of each of the first and second arcuate end portions 24a, 24b is approximately equal to twice the radius $r_1$ of the first and second circular portion 16a, 16b (actually the sum of $r_1$ and $r_2$), and the length of the central portion 22 is twice the radius $r_1$ the central circular portion.

The intersections of adjacent substantially circular sections, e.g., 16a and 16c, define folding axes 26 perpendicular to the longitudinal axis and enlarged flange sections 18a where absorbent structure does not extend between the topsheet and backsheet.

Figure 3:
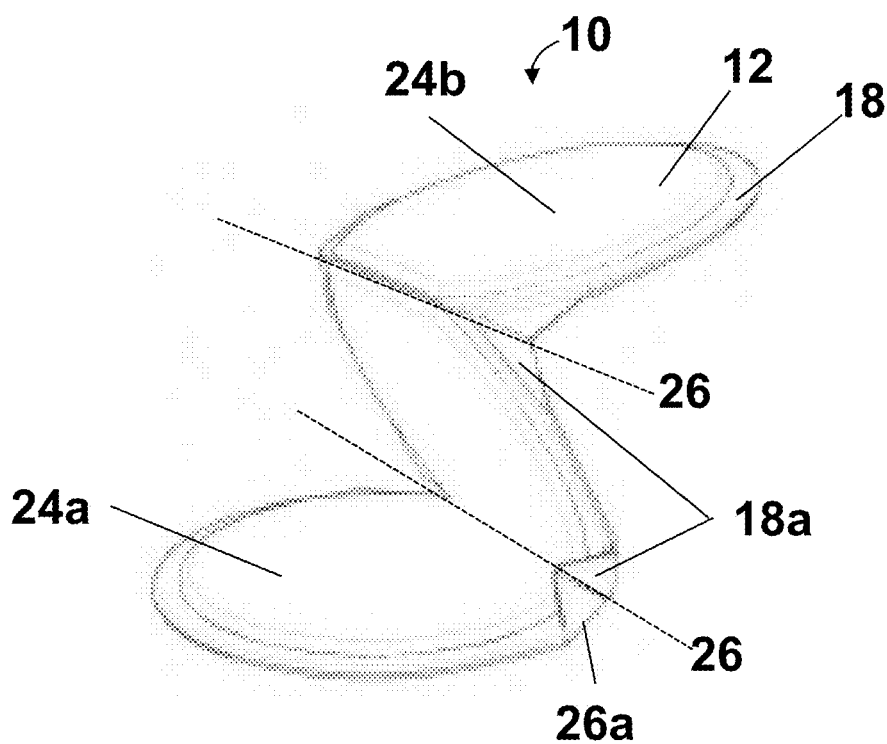
FIG. 3 is a perspective view of an exemplary folding arrangement of the consumer article embodiment of FIG. 1 using two folding axes.
Figure 4:
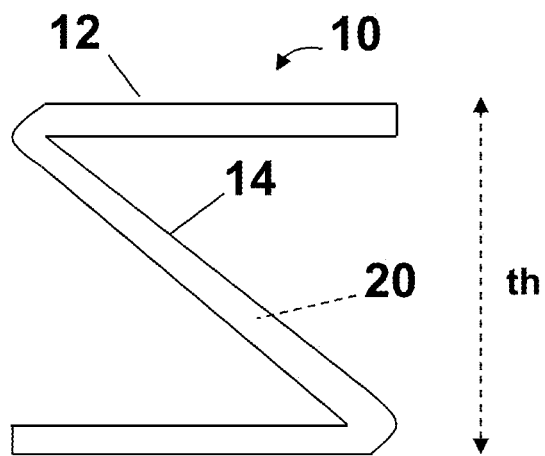
FIG. 4 is a side view of the folding arrangement of the consumer article embodiment of FIG. 1 using two folding axes.
Figure 5:
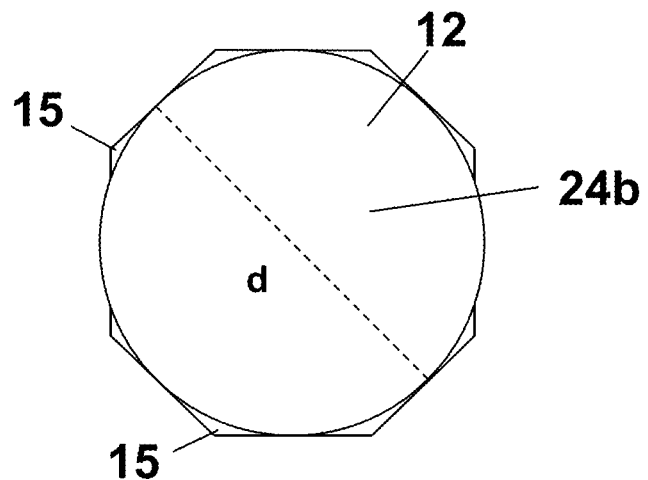
FIG. 5 is a top view of the folded consumer article of FIGS. 3 and 4.
Figure 6:
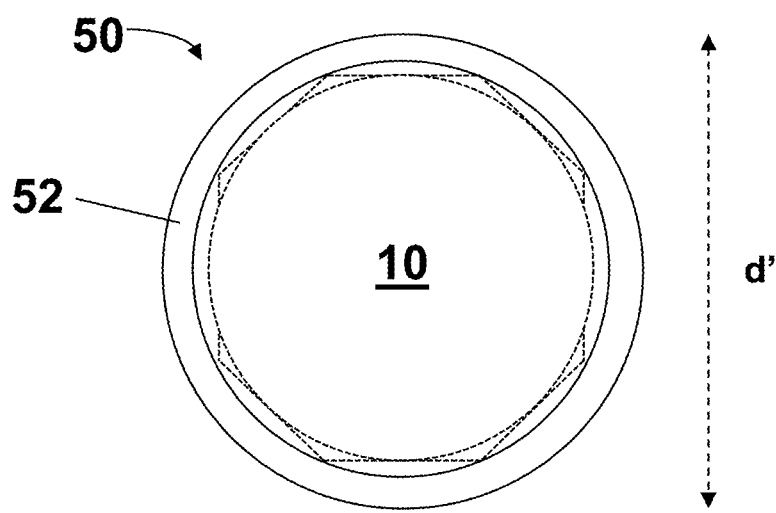
FIG. 6 is a top view of the folded consumer article of FIG. 5 wrapped in thin, circular package.

As shown in FIGS. 3-4, the disposable sanitary article is folded along the two folding axes 26 to prepare for protecting it in a round primary package. In addition, as the absorbent structure does not extend into the enlarged flange sections 18a, these sections can be folded inwardly on secondary folding axes 26a, approximately 45°, to tuck excess portions of the enlarged flange sections 18a toward the interior of the folded product, resulting in a folded sanitary protection article having a generally circular form having a diameter, d, with only minor protrusions 15 of the enlarged flange sections 18a (see FIG. 5). These protrusions 15 are substantially smaller than would have occurred without tucking these portions. In addition, the folded product is substantially thinner than if the absorbent structure filled the enlarged flange sections 18a. As shown in FIG. 6, the folded article can then be enveloped in a circular primary package 50 (as shown in FIG. 6), such as formed by sealing two packing films about a flange 52 around the folded product 10.

While the preceding embodiment can be folded to form a substantially round product for packaging, one of ordinary skill in the art may recognize that the enlarged flange sections 18a penetrate deeply toward the longitudinal axis of the sanitary article and its absorbent structure. This may result in inefficient usage of the absorbent structure.

Figure 7:
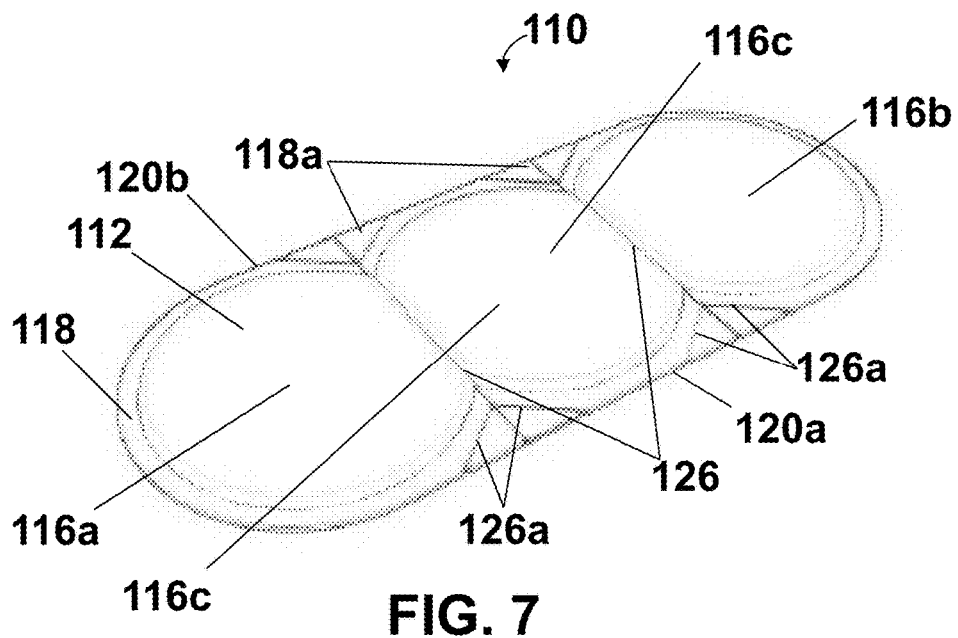
FIG. 7 is a perspective view of a second embodiment of a foldable, round-ended consumer article of the present invention.
Figure 8:
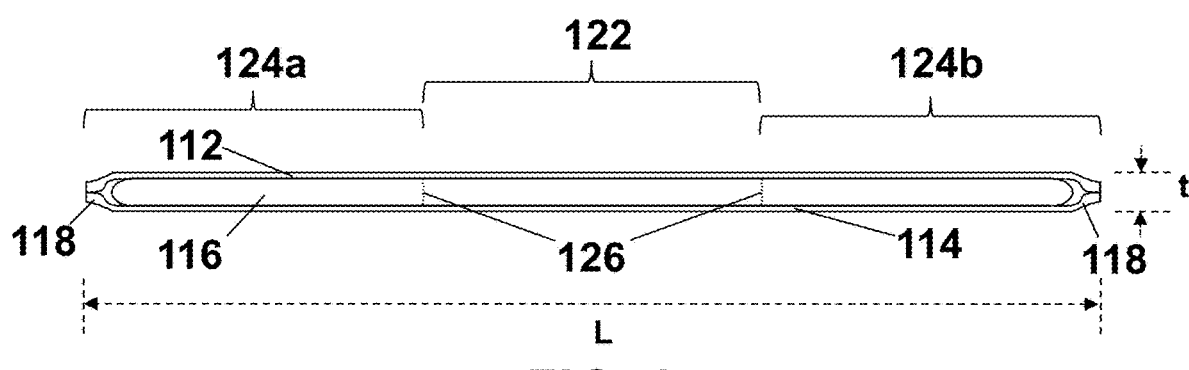
FIG. 8 is a side view of the consumer article embodiment of FIG. 7.
Figure 9:
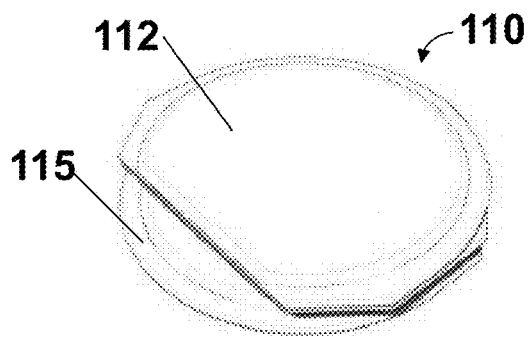
FIG. 9 is a top view of the folded consumer article of FIG. 7 prior to packaging.

The second embodiment of a foldable, round-ended consumer article of the present invention, shown in FIGS. 7-9, minimizes this effect.

As shown in FIGS. 7-9 (perspective and side views of the disposable sanitary article 110 in a use configuration and in a packaged configuration), a preferred embodiment, the foldable, round-ended absorbent sanitary article 110 has a topsheet 112, a backsheet 114, and an absorbent structure 116 therebetween. The topsheet 112 and backsheet 114 are joined together in a flange 118 surrounding the absorbent structure 116. The article has a first longitudinal side 120a, and a longitudinal second side 120b. Article 110 also has a central portion 122 and first and second arcuate end portions 124a and 124b, respectively.

Again, the absorbent structure 116 comprises at least three intersecting, substantially circular sections aligned along the longitudinal axis, a first substantially circular section 116a is associated with the first arcuate end portion 124a and the second substantially circular section 116b associated with the second arcuate end portion 124b. While the embodiment of FIGS. 7-9 includes only three substantially circular portions and the third substantially circular portion 116c is shown in the central portion 122, alternative embodiments, described later, may incorporate additional circular portions of the absorbent structure in an elongated central portion.

Again, the intersections of adjacent substantially circular sections, e.g., 116a and 116c, define folding axes 126 perpendicular to the longitudinal axis and enlarged flange sections 118a where absorbent structure does not extend between the topsheet 112 and backsheet 114.

As shown in FIG. 9, the disposable sanitary article 110 is folded along the two folding axes 126 to prepare for protecting it in a round primary package. In addition, as the absorbent structure does not extend into the enlarged flange sections 118a, these sections can be folded inwardly on secondary folding axes 126a, approximately 45°, to tuck excess portions of the enlarged flange sections 118a toward the interior of the folded product, resulting in a folded sanitary protection article having a generally circular form having a diameter, d, with only minor protrusions 115 of the enlarged flange sections 118a. These protrusions 115 are substantially smaller than would have occurred without tucking these portions. In addition, the folded product is substantially thinner than if the absorbent structure filled the enlarged flange sections 118a. The folded article can then be enveloped in a circular primary package (as shown above in FIG. 6).

Figure 10:
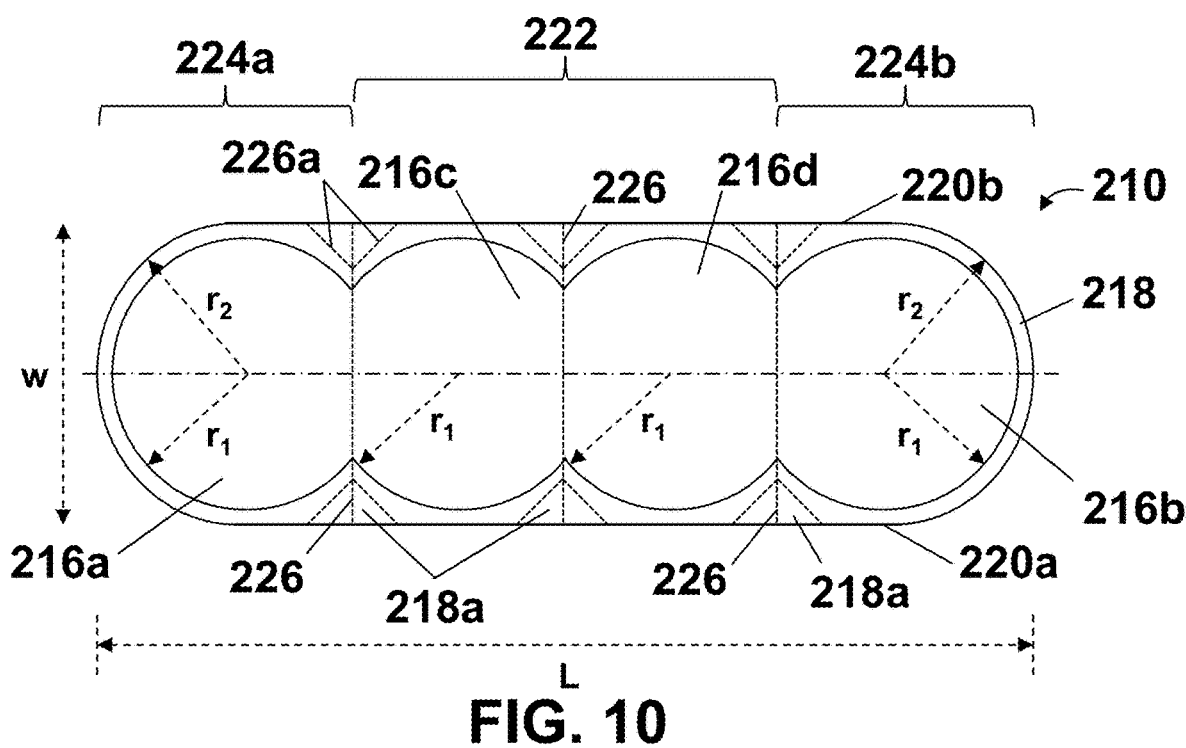
FIG. 10 is a perspective view of a third embodiment of a foldable, round-ended consumer article of the present invention.
Figure 11:
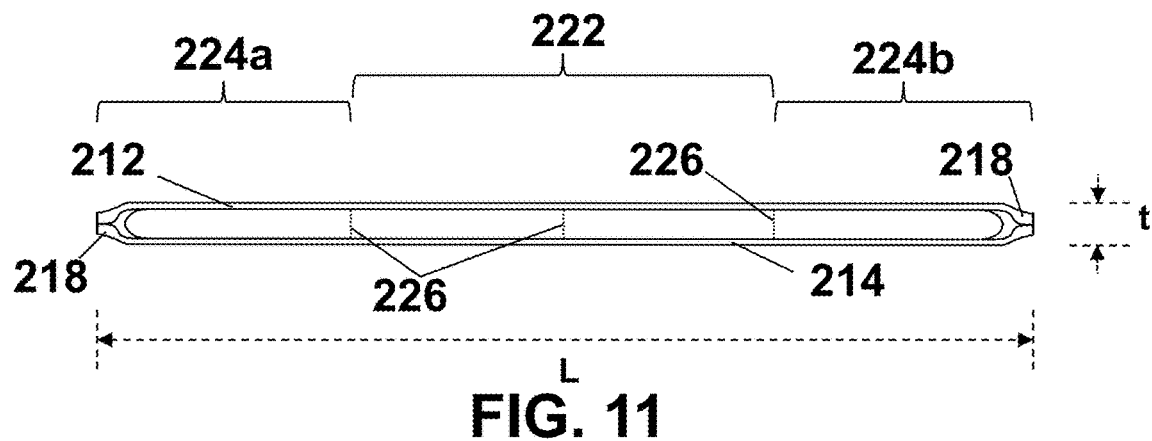
FIG. 11 is a side view of the consumer article embodiment of FIG. 10.
Figure 12:
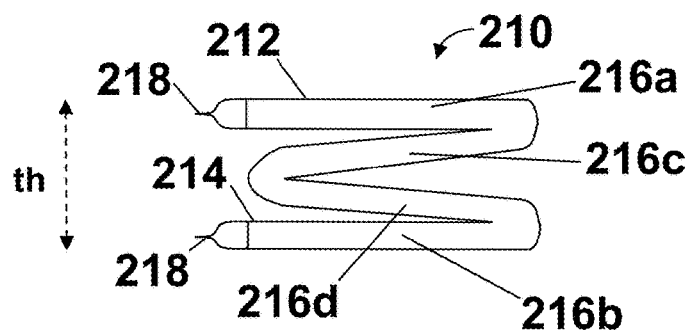
FIG. 12 is a side view of the folded consumer article of FIG. 10 prior to packaging.

A third embodiment of a foldable, round-ended consumer article of the present invention is shown in FIGS. 10-12. As shown in FIGS. 7-9 (perspective and side views of the disposable sanitary article 210 in a use configuration and in a packaged configuration), a preferred embodiment, the foldable, round-ended absorbent sanitary article 210 has a topsheet 212, a backsheet 214, and an absorbent structure 216 therebetween. The topsheet 212 and backsheet 214 are joined together in a flange 218 surrounding the absorbent structure 216. The article has a first longitudinal side 220a, and a longitudinal second side 120b. Article 210 also has a central portion 222 and first and second arcuate end portions 224a and 224b, respectively.

Again, the absorbent structure 216 comprises at least four intersecting, substantially circular sections aligned along the longitudinal axis, a first substantially circular section 216a is associated with the first arcuate end portion 224a and the second substantially circular section 216b associated with the second arcuate end portion 224b. While the embodiment of FIGS. 10-12 includes only four substantially circular portions and the third and fourth substantially circular portions 216c and 216d, respectively, are shown in the central portion 222, alternative embodiments may incorporate additional circular portions of the absorbent structure in an elongated central portion.

Again, the intersections of adjacent substantially circular sections, e.g., 216a and 216c, define folding axes 226 perpendicular to the longitudinal axis and enlarged flange sections 218a where absorbent structure does not extend between the topsheet 212 and backsheet 214.

As shown in FIGS. 10-12, the disposable sanitary article is folded along three folding axes 226 to prepare for protecting it in a round primary package. In addition, as the absorbent structure does not extend into the enlarged flange sections 218a, these sections can be folded inwardly on secondary folding axes 226a, approximately 45°, to tuck excess portions of the enlarged flange sections 218a toward the interior of the folded product, resulting in a folded sanitary protection article having a generally circular form having a diameter substantially that of the first arcuate end portion 224a with only minor protrusions showing around the first arcuate end portion 224a. These protrusions are substantially smaller than would have occurred without tucking the extended flange portions.

While the elongate sanitary protection product has been described above with three or four adjacent substantially circular sections, one of ordinary skill in the art will recognize that the number of substantially circular sections can vary to accommodate any desired length to width ratios. Preferred length to width ratios are between about 2.5 to about 4. More preferred length to with ratios range between about 2.5 and about 3.5.

While the cylindrical package has been described as circular, it can also be in the form of an elliptical or oval cylindrical package, where the top view of the package projects an ellipse or an oval. Package must also have an internal volume sized to receive folded consumer article.

Package could be made of sealable materials such as thin aluminum foil or plastic film. In the case of aluminum foil, the package can be sealed via crimp sealing. Plastic film material can be sealed via heat sealing.

Thickness Measurement:

Thickness of the product can be determined with a thickness gauge applying uniform pressure. A preferred thickness gauge is Ames LG 1820-1-04 or equivalent with a 0.1 psi pressure applied by a 57 g dead weight and a foot surface area of 1.129" of diameter contact; precision is ±0.02 mm or 0.001". The product thickness is measured in the first and second ends and in the center portion. The thickness of the finished product (less any release paper) is measured as follows:

1. Place the release paper (if any) under the foot of the thickness gauge.
2. Re-zero the gauge to remove the thickness of the release paper from the measurements. The gauge should read 0.00 mm (0.000").
3. Reposition the release paper so that it is positioned properly on the adhesive strip and that there are no folds in it, if necessary.
4. Raise the foot of the gauge and place the napkin underneath at the desired position (first and second ends and in the center portion) so that the foot of the gauge hangs above the product.
5. Lower the foot delicately, making sure it does not drop suddenly on the product surface.
6. Allow the gauge to stabilize (approximately 3 seconds), and record the product thickness to the nearest 0.02 mm (0.001").
7. Repeat steps 4 to 6 for each product area to be measured.

While the foregoing description and drawings represent exemplary embodiments of the present invention, it will be understood that various additions, modifications and substitutions may be made therein without departing from the spirit and scope of the present invention. The presently disclosed embodiments are therefore to be considered in all respects as illustrative and not restrictive, the scope of the invention being indicated by the appended claims, and not limited to the foregoing description.

What is claimed is:

1. A packaged elongate sanitary protection product comprising:
    (a) a sanitary protection product comprising a topsheet, a backsheet, and an absorbent structure therebetween and having a longitudinal axis and a thickness, first and second arcuate end portions comprising first and second ends, respectively, separated by a central portion, the arcuate end portions having an effective radius, and a pair of substantially parallel longitudinal side edges connecting the first and second ends;
    wherein
        (i) the topsheet and backsheet are joined together in a flange surrounding the absorbent structure;
        (ii) the absorbent structure comprises at least three intersecting, substantially circular sections aligned along the longitudinal axis, a first substantially circular section associated with the first arcuate end portion and the second substantially circular section associated with the second arcuate end portion and the central portion associated with at least one intervening substantially circular portion;
        (iii) intersections of adjacent substantially circular sections define folding axes perpendicular to the longitudinal axis and enlarged flange sections of the topsheet and backsheet;
        (iv) the sanitary protection product is folded at the fold lines and the enlarged flange sections are additionally folded inwardly, approximately 45° to form a folded sanitary protection product having a generally circular form
    (b) a substantially circular package enveloping the folded sanitary protection product.

2. The packaged product of claim 1 wherein the absorbent structure consists of three intersecting, substantially circular sections, and the sanitary protection product is z-folded.

3. The packaged product of claim 1 wherein the absorbent structure consists of four intersecting, substantially circular sections.

* * * * *